US006355659B1

(12) United States Patent
Merce-Vidal et al.

(10) Patent No.: US 6,355,659 B1
(45) Date of Patent: *Mar. 12, 2002

(54) 4-(4-CHLOROPHENYL)-1236-TETRAHYDRO-1(1H-124-TRIAZOL-1-YL)BUTTY)PYRIDEINE AND SALTS THEREOF; PHARMACEUTICAL COMPOSITIONS AND METHOD OF TREATING PSYCHOSES UTILIZING SAME

(75) Inventors: Ramon Merce-Vidal; Jordi Frigola-Constansa, both of Barcelona; Blas Andaluz-Mataró, Tordera; Josep Mas-Prió, Rubi, all of (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 09/492,640

(22) Filed: Jan. 27, 2000

Related U.S. Application Data

(63) Continuation-in-part of application No. 09/031,024, filed on Feb. 26, 1998, now Pat. No. 6,232,329, which is a continuation of application No. 08/473,066, filed on Jun. 7, 1995, now Pat. No. 5,731,331.

(30) Foreign Application Priority Data

Jul. 29, 1994 (FR) ............................................. 94 09443

(51) Int. Cl.⁷ ........................................... A61K 31/4439

(52) U.S. Cl. ..................................... 514/340; 546/272.4

(58) Field of Search ........................ 546/272.4; 514/340

(56) References Cited

U.S. PATENT DOCUMENTS

| 3,509,153 A | 4/1970 | Hayao et al. |
| 3,994,904 A | 11/1976 | Havera et al. |
| 4,539,407 A | 9/1985 | Stack et al. |
| 4,675,403 A | 6/1987 | Abou-Gharbia et al. |
| 5,227,486 A | 7/1993 | Merce-Vidal et al. ....... 544/295 |
| 4,754,038 A | 6/1998 | Abou-Gharbia et al. |

FOREIGN PATENT DOCUMENTS

| DE | 20 17 265 | 10/1970 |
| DE | 26 32 870 | 2/1977 |
| EP | 0 441 349 A1 | 8/1991 |
| EP | 0 497 658 A1 | 8/1992 |
| EP | 0 497 659 A1 | 8/1992 |

OTHER PUBLICATIONS

CA 74:3627, Welstead.
J. Pharmacol. Exptl. Ther., vol. 148, No. 1, 1965 (p. 54–65)–"Pharmacology of a Group of Phenyliperazine Tetrazole Derivatives with Adrenergic Blocking Actions".
French Search Report of priority French patent application.

*Primary Examiner*—Jane Fan
(74) *Attorney, Agent, or Firm*—Rockey, Milnamow & Katz, Ltd

(57) ABSTRACT

Antipsychotic compound 4-(4-chlorophenyl)-1,2,3,6-tetrahydro-1-[4-(1H-1,2,4-triazol-1-yl) butyl]pyridine, or one of its physiologically acceptable salts, pharmaceutical compositions containing those compounds and a method of treating a disease selected from psychosis and dementias in which a deficit of cognition predominates comprising administering to a patient in need of such treatment a therapeutically effective amount of the antipsychotic compound.

11 Claims, No Drawings

4-(4-CHLOROPHENYL)-1236-TETRAHYDRO-1(1H-124-TRIAZOL-1-YL)BUTTY)PYRIDEINE AND SALTS THEREOF; PHARMACEUTICAL COMPOSITIONS AND METHOD OF TREATING PSYCHOSES UTILIZING SAME

CROSS REFERENCE TO RELATED APPLICATIONS

This application is a continuation-in-part of U.S. application Ser. No. 09/031,024, filed Feb. 26, 1998 now U.S. Pat. No. 6,232,329 which is a continuation of U.S. application Ser. No. 08/473,066 filed Jun. 7, 1995 now U.S. Pat. No. 5,731,331.

FIELD OF THE INVENTION

The present invention relates to 4-(4-chlorophenyl)-1,2,3,6-tetrahydro-1-[4-(1H-1,2,4-triazol-1-yl)butyl]pyridine, of formula

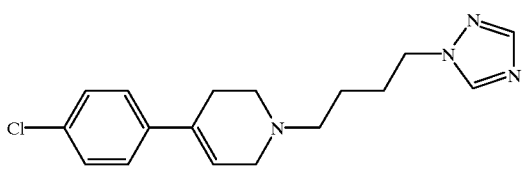

or one of its physiologically acceptable salts, pharmaceutical compositions thereof and their use in the production of medicines for use in human and/or veterinary therapy for the treatment of psychoses.

BACKGROUND OF THE INVENTION

Schizophrenia comprises a heterogeneous group of disorders with various etiological and pathogenic mechanisms. The symptoms of the disease have been classified as positive and negative. The positive symptoms include delirium, hallucinations, paranoia and disorganized behavior and speech. The negative symptoms include loss of energy, speech defects, lack of initiative, loss of sociability and alteration of emotions.

Blocking of the $D_2$ receptor of dopamine is considered to be the basic mechanism of action of the classical antipsychotics, such as haloperidol. However, the clinical efficacy of antagonists of the $D_2$ receptor of dopamine has been shown to be limited, because although they are effective for treating the positive symptoms of the disease, they are not sufficiently effective for treatment of the negative manifestations and moreover they are associated with undesirable effects such as extrapyramidal effects and the development of tardive dyskinesias after prolonged administration.

The search for an "ideal" antipsychotic that would be effective both for the positive and for the negative symptoms but without the undesirable effects of the classical neuroleptics has led to a new generation of antipsychotics known as atypical antipsychotics such as clozapine. However, clozapine has the problem of possible induction of agranulocytosis. Therefore its clinical use has been restricted to the treatment of schizophrenic patients resistant to other treatments, and in addition submitting the patients to regular blood tests for detecting the possible induction of agranulocytosis. These problems in the treatments currently available in human clinical practice were the stimulus for the search for new atypical antipsychotics, with experimental pharmacological activity similar to that of clozapine.

Although this aim has been achieved in part, nevertheless there are no products that are genuinely effective against the negative manifestations of schizophrenia.

In recent years it has been demonstrated that the ligands of the sigma ($\sigma$) receptors have antipsychotic properties both in animal studies [Karbon et al., J. Pharmacol. Exp. Ther., 1993, 265, 866; Maj et al., Eur. J. Pharmacol., 1996, 315, 235; Akunne, Neuropharmacology, 1997, 36, 51] and in clinical trials [Snyder et al., J. Neuropsychiatry Clin. Neurosci., 1989, 1, 7; Frboes et al., Psychopharmacology, 1997, 132, 82] with a negligible incidence of extrapyramidal effects. In the sigma ($\sigma$) receptors, two subtypes have been identified and characterized pharmacologically: $\sigma_1$ and $\sigma_2$.

Compounds of the following general formula are described in our U.S. Pat. No. 5,731,331 and divisional patent application U.S. application Ser. No. 09/031,024, filed on Feb. 26, 1998.

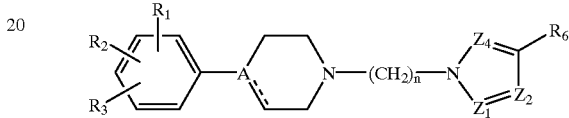

which have affinity for the a and $5HT_{1A}$ receptors, and are claimed as medicines that can be used in the treatment of anxiety, psychoses, epilepsy, convulsion, amnesia, cerebrovascular diseases and senile dementia. The disclosures of the above-mentioned patent and application are incorporated herein by reference.

We have now found that the compound 4-(4-chlorophenyl)-1,2,3,6-tetrahydro-1-[4-(1H-1,2,4-triazol-1-yl)butyl]pyridine, as well as its physiologically acceptable salts, have great affinity for the $\sigma$ receptors, and especially for the $\sigma_1$ receptor. Moreover, their pharmacological properties indicate that they are atypical antipsychotics with particular properties with respect to the negative manifestations that are superior to the products developed up to now, and therefore these compounds are especially useful for the production of medicines, in human and/or veterinary therapy, for the treatment of psychoses.

BRIEF SUMMARY OF THE INVENTION

The present invention relates to 4-(4-chlorophenyl)-1,2,3,6-tetrahydro-1-[4-(1H-1,2,4-triazol-1-yl)butyl]pyridine, of formula

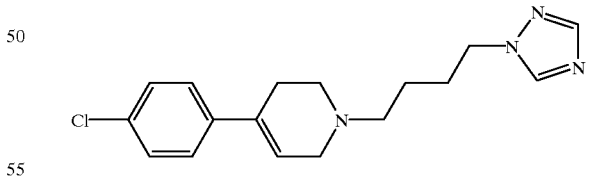

or one of its physiologically acceptable salts, pharmaceutical compositions thereof and their use in the production of medicines that can be used in human and/or veterinary therapy for the treatment of psychoses.

DETAILED DESCRIPTION OF THE INVENTION

Physiologically acceptable salts of the compound 4-(4-chlorophenyl)-1,2,3,6-tetrahydro-1-[4-(1H-1,2,4-triazol-1-yl)butyl]pyridine refer both to the salts formed with inorganic acids and with organic acids, in particular to the salts of hydrochloric, hydrobromic, sulfuric, phosphoric, acetic, lactic, masonic, succinic, glutaric, fumaric, malic, tartaric, citric, ascorbic, maleic, benzoic, phenylacetic, cinnamic, and salicylic acids, and alkyl, cycloalkyl or arylsulfonic acids, such as methanesulfonic or p-toluenesulfonic acids.

The use of 4-(4-chlorophenyl)-1,2,3,6-tetrahydro-1-[4-(1H-1,2,4-triazol-1-yl)butyl]pyridine, or one of its physiologically acceptable salts, for the treatment of psychoses refers to their use as antipsychotics in clinical practice.

There now follow some examples of production of 4-(4-chlorophenyl)-1,2,3,6-tetrahydro-1-[4-(1H-1,2,4-triazol-1-yl)butyl]pyridine and of some of its physiologically acceptable salts, as well as some examples of biological activity, given purely for illustration, it being understood that they can in no way limit the specific conditions of the process nor the scope of the invention.

EXAMPLE 1

Preparation of 4-(4-chlorophenyl)-1,2,3,6-tetrahydro-1-[4-(1H-1,2,4-triazol-1-yl)butyl]pyridine A mixture of 4-(4-chlorophenyl)-1,2,3,6-tetrahydropyridine hydrochloride (48.5 g, 0.21 mol), 1-(4-chlorobutyl)triazole (35 g, 0.21 mol), acid carbonate of potassium (105 g, 1.05 mol) and sodium iodide (6 g) in acetonitrile (500 ml) is heated under reflux for 24 hours. Once it is cold, water is added and the two phases are separated. The organic phase is dried with anhydrous sodium sulfate and is evaporated under reduced pressure. 54.5 g of a product are obtained which, when recrystallized in acetonitrile, yields 51 g (77%) of 4-(4-chlorophenyl)-1,2,3,6-tetrahydro-1-[4-(1H-1,2,4-triazol-1-yl)butyl]pyridine of m.p. 101–3° C.

IR (KBr, $cm^{-1}$): 2930, 2775, 2737, 1509, 1493, 1381, 1271, 1141, 1091, 1010, 961, 847, 828, 680

$^1$H-NMR [300 MHz, $CDCl_3$, 25° C., δ(ppm)]: 1.56 (quint, J=7.5 Hz, 2H); 1.97 (quint, J=7.5 Hz, 2H); 2.40–2.70 (a.c., 4H); 2.66 (t, J=5.7 Hz, 2H); 3.10 (d, J=3 Hz, 2H), 4.21 (t, J=7.0 Hz, 2H); 6.04 (s, 1H); 7.20–7.35 (m, 4H); 7.94 (s, 1H); 8.06 (s, 1H)

EXAMPLE 2

Preparation of the hydrochloride of 4-(4-chlorophenyl)-1,2,3,6-tetrahydro-1-[4-(1H-1,2,4-triazol-1-yl)butyl]pyridine A solution of ethanol/hydrochloric acid (6.8 ml, 6 N) is added to a solution of 4-(4-chlorophenyl)-1,2,3,6-tetrahydro-1-[4-(1H-1,2,4-triazol-1-yl)butyl]pyridine (11.5 g, 36.3 mmol) in absolute ethanol (50 ml) cooled on an ice bath. After a few minutes ethyl ether (200 ml) is added and a precipitate appears, which is filtered, washed with cold ethanol and dried, yielding 12 g (93%) of 4-(4-chlorophenyl)-1,2,3,6-tetrahydro-1-[4-(1H-1,2,4-triazol-1-yl)butyl]pyridine hydrochloride of m.p. 165–6° C.

IR (KBr, $cm^{-1}$): 2951, 2505 (b.a.) 1502, 1494, 1275, 1136, 1098, 1013, 810, 686

$^1$H-NMR [300 MHz, DMSO-$d_6$, 25° C., δ(ppm)]: 1.73 (m, 2H); 1.83 (m, 2H); 2.70 (m, 1H); 2.85 (m, 1H); 3.10–3.20 (a.c., 3H); 3.54 (m, 1H); 3.73 (m, 1H); 3.88 (m, 1H), 4.22 (t, J=6.6 Hz, 2H); 6.20 (s, 1H); 7.42 (AB, J=8.6 Hz, 2H); 7.49 (AB, J=8.6 Hz, 2H); 7.97 (s, 1H); 8.59 (s, 1H)

EXAMPLE 3

Preparation of the citrate of 4-(4-chlorophenyl)-1,2,3,6-tetrahydro-1-[4-(1H-1,2,4-triazol-1-yl)butyl]pyridine A solution of citric acid monohydrate (33.8 g, 0.16 mol) in water (30 ml) is added to a solution of 4-(4-chlorophenyl)-1,2,3,6-tetrahydro-1-[4-(1H-1,2,4-triazol-1-yl)butyl]pyridine (51 g, 0.16 mol) in absolute ethanol (350 ml) at 40° C. After about 20 minutes a precipitate appears, which is filtered after cooling to room temperature, washed with cold ethanol and dried, yielding 68.9 g (84%) of 4-(4-chlorophenyl)-1,2,3,6-tetrahydro-1-[4-(1H-1,2,4-triazol-1-yl)butyl]pyridine citrate of m.p. 133–4° C.

IR (KBr, $cm^{-1}$): 3384 (b.a.), 3200–2200 (b.a.) 1726, 1702, 1594, 1432, 1221, 1131, 802

$^1$H-NMR [300 MHz, DMSO-$d_6$, 25° C., δ(ppm)]: 1.54 (m, 2H); 1.83 (m, 2H); 2.54 (AB, J=15 Hz, 2H); 2.63 (AB, J=15 Hz, 2H); 2.82 (m, 2H); 3.03 (m, 2H); 3.20–3.50 (a.c., 4H); 4.21 (t, J=6.8 Hz, 2H); 6.20 (s, 1H); 7.40 (AB, J=8.8 Hz, 2H); 7.48 (AB, J=8.8 Hz, 2H); 7.97 (s, 1H); 8.52 (s, 1H)

EXAMPLE 4

Preparation of the fumarate of 4-(4-chlorophenyl)-1,2,3,6-tetrahydro-1-[4-(1-1,2,4-triazol-1-yl)butyl]pyridine A solution of fumaric acid (0.464 g, 4 mmol) in absolute ethanol (10 ml) is added to a solution of 4-(4-chlorophenyl)-1,2,3,6-tetrahydro-1-[4-(1H-1,2,4-triazol-1-yl)butyl]pyridine (1.26 g, 4 mmol) in isopropanol (12 ml) at 40° C. After about 20 minutes a precipitate appears, which is filtered after cooling to room temperature, washed with cold ethanol and dried, yielding 1.65 g (93%) of 4-(4-chlorophenyl)-1,2,3,6-tetrahydro-1-[4-(1H-1,2,4-triazol-1-yl)butyl]pyridine fumarate of m.p. 156–9° C.

IR (KBr, $cm^{-1}$): 2940 (b.a.), 2418, 1697, 1508, 1496, 1272, 1162, 678

$^1$H-NMR [300 MHz, DMSO-$d_6$/TFA, 25° C., δ(ppm)]: 1.65 (m, 2H); 1.82 (m, 2H); 2.74 (m, 2H); 3.18 (m, 3H); 3.61–3.76 (a.c, 2H); 3.95 (m, 1H); 4.26 (t, J=6.6 Hz, 2H); 6.21 (s, 1H); 6.61 (s, 2H) ; 7.50 (AB, J=8.5 Hz, 2H); 7.43 (AB, J=8.5 Hz, 2H); 8.18 (s, 1H); 8.78 (s, 1H)

EXAMPLE 5

Preparation of the sulfate of 4-(4-chlorophenyl)-1,2,3,6-tetrahydro-1-[4-(1H-1,2,4-triazol-1-yl)butyl]pyridine A solution of 96% sulfuric acid (0.196 g) in isopropanol (2 ml) is added to a solution of 4-(4-chlorophenyl)-1,2,3,6-tetrahydro-1-[4-(1H-1,2,4-triazol-1-yl)butyl]pyridine (0.63 g, 2 mmol) in isopropanol (6 ml) cooled on an ice bath. After a few minutes a precipitate appears, which is filtered, washed with cold ethanol and dried, yielding 0.74 g (90%) of 4-(4-chlorophenyl)-1,2,3,6-tetrahydro-1-[4-(1H-1,2,4-triazol-1-yl)butyl]pyridine sulfate of m.p. 164–6° C.

IR (KBr, $cm^{-1}$): 2958 (b.a.), 2570 (b.a.), 1536, 1492, 1430, 1112, 983, 803, 617

$^1$H-NMR [300 MHz, DMSO-$d_6$/TFA, 25° C., δ(ppm)]: 1.66 (m, 2H); 1.85 (m, 2H); 2.74 (m, 2H); 3.19 (m, 3H); 3.61–3.76 (a.c., 2H); 3.98 (m, 1H); 4.28 (t, J=6.6 Hz, 2H); 6.21 (s, 1H); 7.50 (AB, J=8.6 Hz, 2H); 7.43 (AB, J=8.6 Hz, 2H); 8.26 (s, 1H); 8.89 (s, 1H)

EXAMPLE 6

Preparation of the phosphate of 4-(4-chlorophenyl)-1,2,3,6-tetrahydro-1-[4-(1H-1,2,4-triazol-1-yl)butyl]pyridine A solution of 85% phosphoric acid (0.225 g, 2 mmol) in isopropanol (1 ml) is added to a solution of 4-(4- chlorophenyl)-1,2,3,6-tetrahydro-1-[4-(1H-1,2,4-triazol-1-yl)butyl]pyridine (0.63 g, 2 mmol) in isopropanol (6 ml) cooled on an ice bath. After a few minutes a precipitate appears, which is filtered, washed with cold ethanol and dried, yielding 0.77 g (93%) of 4-(4-chlorophenyl)-1,2,3,6-tetrahydro-1-[4-(1H-1,2,4-triazol-1-yl)butyl]pyridine phosphate of m.p. 146–8° C.

IR (KBr, cm$^{-1}$): 3422 (b.a.), 1508, 1492, 1274, 1094, 1059, 1011, 943, 808

$^1$H-NMR [300 MHz, DMSO-d$_6$/TFA, 25° C., δ(ppm)]: 1.65 (m, 2H); 1.84 (m, 2H); 2.74 (m, 2H); 3.18 (m, 3H); 3.61–3.78 (a.c., 2H); 3.96 (m, 1H); 4.25 (t, J=6.6 Hz, 2H); 6.22 (s, 1H); 7.51 (AB, J=8.6 Hz, 2H); 7.43 (AB, J=8.6 Hz, 2H); 8.08 (s, 1H); 8.66 (s, 1H)

EXAMPLE 7

Preparation of the methanesulfonate of 4-(4-chlorophenyl)-1,2,3,6-tetrahydro-1-[4-(1H-1,2,4-triazol-1-yl)butyl]pyridine A solution of methanesulfonic acid (0.63 g, 2 mmol) in acetone (1 ml) is added to a solution of 4-(4-chlorophenyl)-1,2,3,6-tetrahydro-1-[4-(1H-1,2,4-triazol-1-yl)butyl]pyridine (0.63 g, 2 mmol) in acetone (5 ml) at 40° C. After about 20 minutes a precipitate appears, which is filtered after cooling to room temperature, washed with cold ethanol and dried, yielding 0.66 g (80%) of 4-(4-chlorophenyl)-1,2,3,6-tetrahydro-1-[4-(1H-1,2,4-triazol-1-yl)butyl]pyridine methanesulfonate of m.p. 130–2° C.

IR (KBr, cm$^{-1}$): 3432 (b.a.), 2934 (b.a.), 2584, 1508, 1494, 1239, 1194, 1058, 784

$^1$H-NMR [300 MHz, DMSO-d$_6$/TFA, 25° C., δ(ppm)]: 1.65 (m, 2H); 1.83 (m, 2H); 2.39 (s, 3H); 2.74 (m, 2H); 3.19 (m, 3H); 3.61–3.78 (a.c., 2H); 3.98 (m, 1H); 4.27 (t, J=6.6 Hz, 2H); 6.21 (s, 1H); 7.50 (AB, J=8.5 Hz, 2H); 7.43 (AB, J=8.5 Hz, 2H); 8.21 (s, 1H); 8.83 (s, 1H)

Pharmacological investigation of the antipsychotics comprises a wide range of tests with the aim of establishing both the antipsychotic activity in its aspects of efficacy against the stated positive symptoms and negative manifestations of schizophrenia, and the capacity to induce undesirable extrapyramidal effects. Within this range of tests, two of them stand out as most used in the evaluation of antipsychotics: antagonism of the climbing activity induced by apomorphine and the induction of catalepsy. Activity against the negative manifestations is identified by demonstrating activation of brain areas involved in cognitive processes, such as the medial area of the prefrontal cortex.

Antagonism of the climbing activity induced by apomorphine in the mouse [T. G. Heffner et al., J. Pharmacol. Exp. Ther., 1989, 251, 105] is one of the tests that most clearly define antipsychotic activity, both of the typical antipsychotics and of the atypical antipsychotics.

The induction of catalepsy in rats [J. Robert et al., J. Pharmacol. Exp. Ther., 1986, 239, 124] is a parameter that is commonly employed for determining the ability of antipsychotics to induce extrapyramidal effects. The typical antipsychotics are those which, in spite of being very powerful in specific tests of antipsychotic activity, induce extrapyramidal effects, and this is detected in the catalepsy test. The best known of the typical antipsychotics is haloperidol, whereas the best known of the atypical antipsychotics is clozapine.

The compound of Example 2 demonstrated an antipsychotic activity similar to that of clozapine (DE-50=14 mg/kg, i.p.) with complete absence of cataleptic effects at doses up to 80 mg/kg, s.c. This contrasts with the results for haloperidol, which although possessing good antipsychotic activity (DE-50=0.13 mg/kg, i.p.), has very high cataleptic activity, of the same order as the antipsychotic (DE-50=0.14 mg/kg, s.c.).

| Compound | Inhibition of the climbing activity induced by apomorphine | Induction of catalepsy |
| --- | --- | --- |
| Example 2 | DE-50 = 14 mg/kg, i.p. | Inactive up to 80 mg/kg, s.c. |
| Clozapine | DE-50 = 14 mg/kg, i.p. | Inactive up to 80 mg/kg, s.c. |
| Haloperidol | DE-50 = 0.13 mg/kg, i.p. | DE-50 = 0.14 mg/kg, s.c. |

Therefore the advantage of the compound of Example 2 relative to the typical antipsychotics, such as haloperidol, is that as well as notable antipsychotic activity it does not induce catalepsy, which indicates absence of extrapyramidal effects. Comparing it with clozapine, an atypical antipsychotic that is of limited use owing to possible induction of agranulocytosis, we see that the compound of Example 2 has the same profile of antipsychotic activity, both of potency an d of absence of induction of extrapyramidal effects.

Induction of the Protein c-fos in Various Brain Areas in the Rat

The results of this study confirm the antipsychotic activity and the absence of extrapyramidal effects of the compound of Example 2. In addition they indicate its activity against the negative symptom of schizophrenia, demonstrating both antipsychotic potency and potency against the negative symptoms, greater than clozapine.

Acute treatment with various antipsychotics is characterized by the induction of the protein c-fos, owing to the rapid induction off the c-fos gene in various areas of the limbic and extrapyramidal systems [M. Dragunow et al., Neuroscience, 1990, 37, 287–294; J. C. Miller, J. Neurochem., 1990, 54, 1453–1455; A. Y. Deutch et al., Mol. Cell. Neurosci., 1992, 3, 332–341; T. V. Nguyen et al., Proc. Natl. Acad. Sci. USA, 1992, 89, 4270–4274; G. S. Robertson and H. C. Fibinger, Neuroscience, 1992, 46, 315–328]. The patterns of induction of the protein depend on whether the antipsychotic is typical or atypical [G. S. Robertson et al., J. Pharmacol. Exp. Ther., 1994, 271, 1058–1066; G. S. Robertson and H. C. Fibinger, Neuroscience, 1992, 46, 315–328]. These changes in expression of c-fos can be investigated by extraction of the proteins from the brain areas of interest, and analysis of the levels by electrophoresis (Western blot).

Acute treatment with the compound of Example 2, at a dose of just 20 mg/kg s.c., induced a significant increase in the levels of Fos in the nucleus accumbens and in the medial area of the prefrontal cortex (118% and 134% of the group injected with saline, respectively). On the other hand the levels of Fos did not change significantly in the dorsolateral groove on administering the compound of Example 2 (104% of the saline group).

The administration of clozapine exhibited some similar effects, both in the prefrontal cortex (134%) and in the nucleus accumbens and in the dorsolateral groove (118% and 110%), but we must emphasize that a much higher dose was determined for it (30 mg/kg, s.c.).

Control of immunoreactivity of the Fos protein by acute treatment

| Compound | Dose (mg/kg, s.c) | Fos immunoreactivity % change relative to control | | |
|---|---|---|---|---|
| | | Dorsolateral groove | Nucleus accumbens | Medial area of prefrontal cortex |
| Example 2 | 20 | 104% (NS) | 118% (*) | 134% (***) |
| Clozapine | 30 | 110% (NS) | 118% (*) | 130% (*) |

The nucleus accumbens is the only brain region in which the expression of c-fos increases after administration of any of the known antipsychotics, suggesting that it might be a critical site for antipsychotic activity.

On the other hand, only the administration of few atypical antipsychotics induces an increase in the number of immunoreactive cells of the Fos type, in the medial zone of the prefrontal cortex. It has been suggested that hypofrontality is associated with the negative symptoms of schizophrenia [K. F. Berman et al., *Arch. Gen. Psychiatry*, 1986, 43, 126–135; D. R. Weinberger, *Trends Neurosci.*, 1988, 8, 367–370], hence the antipsychotics capable of increasing expression of c-fos in this brain area will be active in the treatment of the negative signs.

Both effects are observed both with clozapine and with the compound of Example 2, but at different doses (30 and 20 mg/kg, s.c., respectively), thus demonstrating that the compound of Example 2 is more powerful than clozapine in both effects, both in relation to antipsychotic activity and in relation to activity against the negative symptoms of schizophrenia On the other hand, the compound of Example 2 does not induce any significant change in levels of Fos in the dorsolateral groove, which is an indication that it is without extrapyramidal side effects, at the same dose that it displays antipsychotic effects and moreover with possible efficacy against the negative symptoms of schizophrenia.

| Receptor | Ki |
|---|---|
| 5-HT1A | 600 nM |
| SIGMA-1 ($\sigma_1$) | 3.7 nM |
| SIGMA-2 ($\sigma_2$) | 465 nM |

In human therapy, the dose of administration of the compounds of the present invention is a function of the severity of the disorder to be treated. Normally it will be between 1 and 100 mg/day. The compounds of the invention, with a suitable pharmaceutical formulation, will be administered by various routes such as oral, transdermal, parenteral, subcutaneous, intranasal, intramuscular or intravenous. As an example, the following is the pharmaceutical composition of a tablet containing a product of the invention.

| Example 3 | 5 mg |
|---|---|
| Lactose | 60 mg |
| Crystalline cellulose | 25 mg |
| Providone K 90 | 5 mg |
| Pregelatinized starch | 3 mg |
| Colloidal silica | 1 mg |
| Magnesium stearate | 1 mg |
| Total weight | 100 mg |

What is claimed is:

1. A method of treating a disease selected from psychosis and dementias in which a deficit of cognition predominates comprising administering to a patient in need of such treatment a therapeutically effective amount of the compound 4-(4-chlorophenyl)-1,2,3,6-tetrahydro-1-[4-(1H-1,2,4-triazol-1-yl)butyl]pyridine, of formula

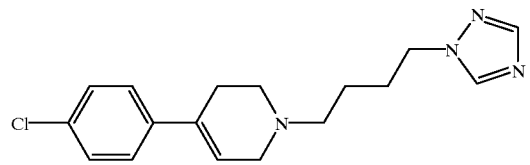

or one of its physiologically acceptable salts.

2. The method as in claim 1 wherein the compound is 4-(4-chlorophenyl)-1,2,3,6-tetrahydro-1-[4-(1H-1,2,4-triazol-1-yl)butyl]pyridine hydrochloride.

3. The method as in claim 1 wherein the compound is 4-(4-chlorophenyl)-1,2,3,6-tetrahydro-1-[4-(1H-1,2,4-triazol-1-yl)butyl]pyridine citrate.

4. The method as claimed in claim 1 wherein the compound is 4-(4-chlorophenyl)-1,2,3,6-tetrahydro-1-[4-(1H-1,2,4-triazol-1-yl)butyl]pyridine fumarate.

5. The method as in claim 1 wherein the compound is 4-(4-chlorophenyl)-1,2,3,6-tetrahydro-1-[4-(1H-1,2,4-triazol-1-yl)butyl]pyridine sulfate.

6. The method as in claim 1 wherein the compound is 4-(4-chlorophenyl)-1,2,3,6-tetrahydro-1-[4-(1H-1,2,4-triazol-1-yl)butyl]pyridine phosphate.

7. The method as in claim 1 wherein the compound is 4-(4-chlorophenyl)-1,2,3,6-tetrahydro-1-[4-(1H-1,2,4-triazol-1-yl)butyl]pyridine methanesulfonate.

8. 4-(4-chlorophenyl)-1,2,3,6-tetrahydro-1-[4-(1H-1,2,4-triazol-1-yl)butyl]pyridine, of formula

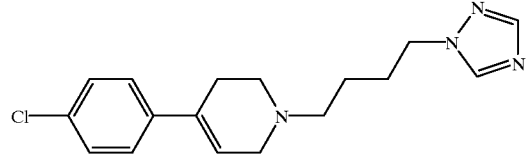

or one of its physiologically acceptable salts.

9. A compound of claim 1 selected from the group consisting of 4-(4-chlorophenyl)-1,2,3,6-tetrahydro-1-[4-(1H-1,2,4-triazol-1-yl)butyl]pyridine hydrochloride, 4-(4-chlorophenyl)-1,2,3,6-tetrahydro-1-[4-(1H-1,2,4-triazol-1-yl)butyl]pyridine citrate, 4-(4-chlorophenyl)-1,2,3,6-tetrahydro-1-[4-(1H-1,2,4-triazol-1-yl)butyl]pyridine fumarate, 4-(4-chlorophenyl)-1,2,3,6-tetrahydro-1-[4-(1H-1,2,4-triazol-1-yl)butyl]pyridine sulfate, 4-(4-chlorophenyl)-1,2,3,6-tetrahydro-1-[4-(1H-1,2,4-triazol-1-yl)butyl]pyridine phosphate and 4-(4-chlorophenyl)-1,2,3,6-tetrahydro-1-[4-(1H-1,2,4-triazol-1-yl)butyl]pyridine methanesulfonate.

10. A pharmaceutical composition comprising:
   a compound of claim 8 in a pharmaceutically acceptable carrier.

11. A pharmaceutical composition comprising:
   a compound of claim 9 in a pharmaceutically acceptable carrier.

* * * * *

UNITED STATES PATENT AND TRADEMARK OFFICE
CERTIFICATE OF CORRECTION

PATENT NO. : 6,355,659 B1
DATED : March 12, 2002
INVENTOR(S) : Merce-Vidal et al.

It is certified that error appears in the above-identified patent and that said Letters Patent is hereby corrected as shown below:

Title page,
Item [54], Title, change "4-(4-CHLOROPHENYL)-1236-TETRAHYDRO-1(1H-124-TRIAZOL-1-YL)BUTTY)PYRIDEINE AND SALTS THEREOF; PHARMACEUTICAL COMPOSITIONS AND METHOD OF TREATING PSYCHOSES UTILIZING SAME" to -- 4-(4-CHLOROPHENYL)-1,2,3,6-TETRAHYDRO-1-[4-(1H-1,2,4-TRIAZOL-1-yl)BUTYL]PYRIDINE AND SALTS THEREOF; PHARMACEUTICAL COMPOSITIONS AND METHOD OF TREATING PSYCHOSES UTILIZING SAME --.

Signed and Sealed this

Twenty-ninth Day of June, 2004

JON W. DUDAS
*Acting Director of the United States Patent and Trademark Office*